United States Patent [19]
Sirhan et al.

[11] Patent Number: 5,496,275
[45] Date of Patent: Mar. 5, 1996

[54] LOW PROFILE DILATATION CATHETER

[75] Inventors: Motasim M. Sirhan, Sunnyvale; Jovito L. Fernando, Modesto, both of Calif.

[73] Assignee: Advanced Cardiovascular Systems, Inc., Santa Clara, Calif.

[21] Appl. No.: 192,065

[22] Filed: Feb. 4, 1994

Related U.S. Application Data

[63] Continuation of Ser. No. 95,814, Jul. 20, 1993, abandoned, and Ser. No. 21,062, Apr. 15, 1993, abandoned, which is a continuation of Ser. No. 700,617, May 15, 1991, abandoned, said Ser. No. 95,814, is a continuation of Ser. No. 700,617.

[51] Int. Cl.⁶ .................................................. A61M 29/00
[52] U.S. Cl. ............................ 604/96; 604/264; 604/102
[58] Field of Search ........................... 128/772, 656–658; 606/192–194; 604/43, 96–103, 173, 258, 264, 280, 282

[56] References Cited

U.S. PATENT DOCUMENTS

| | | | |
|---|---|---|---|
| 2,248,934 | 7/1941 | Auzin | 604/103 |
| 2,457,244 | 12/1948 | Lamson | 604/96 |
| 2,912,981 | 11/1959 | Keough | 604/98 |
| 3,112,748 | 12/1963 | Colburn | 128/350 R |
| 3,983,879 | 10/1976 | Todd | 604/96 |
| 4,295,464 | 10/1981 | Sohata | 604/98 |
| 4,553,959 | 11/1985 | Hickey et al. | 604/96 |
| 4,563,170 | 1/1986 | Aigner | 604/43 |
| 4,723,936 | 2/1988 | Buchbinder et al. | 604/96 |
| 4,748,982 | 6/1988 | Horzewski et al. | 606/192 |
| 4,771,777 | 9/1988 | Horzewski et al. | 604/101 |
| 4,790,315 | 12/1988 | Mueller, Jr. et al. | 606/194 |
| 4,850,373 | 7/1989 | Zatloukal et al. | 604/44 |
| 4,877,031 | 10/1989 | Conway et al. | 604/96 |
| 4,892,519 | 1/1990 | Songer et al. | 604/96 |
| 4,906,230 | 3/1990 | Maloney et al. | 604/95 |
| 4,917,666 | 4/1990 | Solar et al. | 604/96 |
| 4,943,278 | 7/1990 | Euteneuer et al. | 606/194 |
| 4,944,745 | 7/1990 | Sogard et al. | 604/103 |
| 4,998,923 | 3/1991 | Samson et al. | 604/95 |
| 5,037,386 | 8/1991 | Marcus et al. | 604/43 |
| 5,040,548 | 8/1991 | Yock | 128/898 |
| 5,046,503 | 9/1991 | Schneiderman | 606/194 |
| 5,102,390 | 4/1992 | Crihenden et al. | 606/194 |
| 5,149,330 | 9/1992 | Brightbill | 604/280 |
| 5,156,594 | 10/1992 | Keith | 604/96 |
| 5,172,222 | 12/1992 | Euteneuer et al. | 604/102 |

FOREIGN PATENT DOCUMENTS 3522782  1/1987  Germany ................. 604/44

*Primary Examiner*—Corrine M. Maglione
*Assistant Examiner*—N. Kent Gring
*Attorney, Agent, or Firm*—Crosby, Heafey, Roach & May

[57]  ABSTRACT

An intravascular catheter, such as a balloon dilatation catheter, which has a distal section wherein a small dimensioned distal section of an outer tubular member is bonded to an inner tubular member over a significant portion thereof to provide a catheter shaft having small transverse dimensions and improved flexibility with little or no loss is pushability. The catheter construction can be employed in a wide variety of catheters.

28 Claims, 3 Drawing Sheets

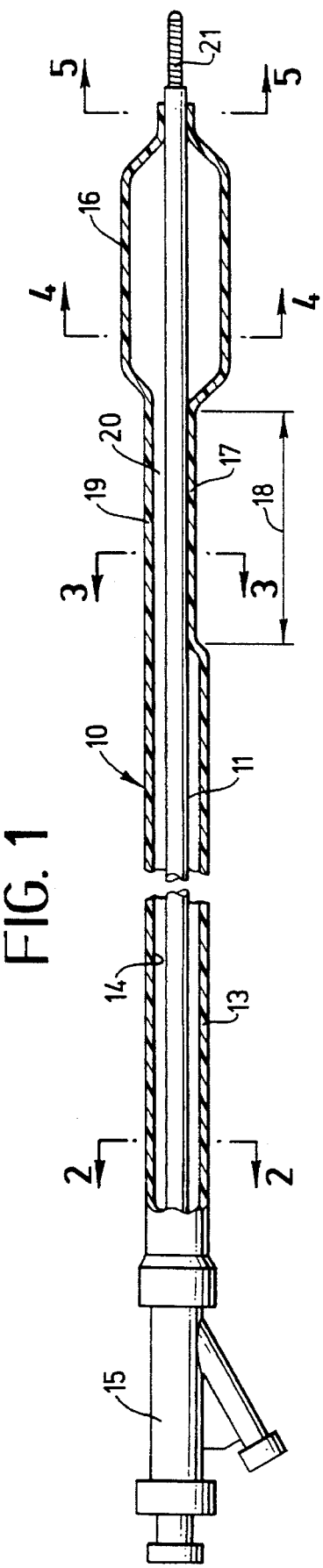

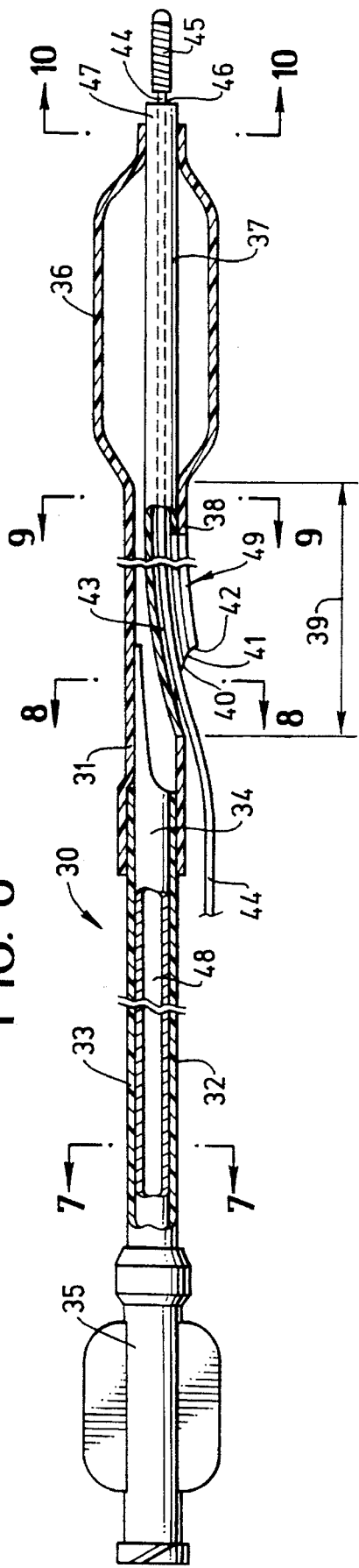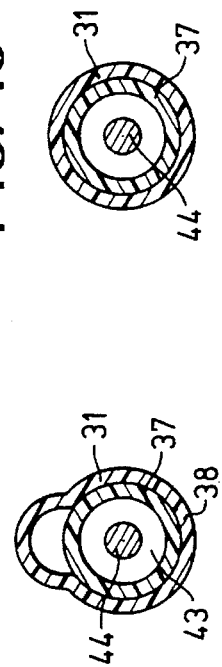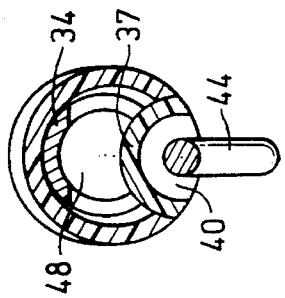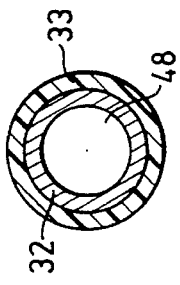

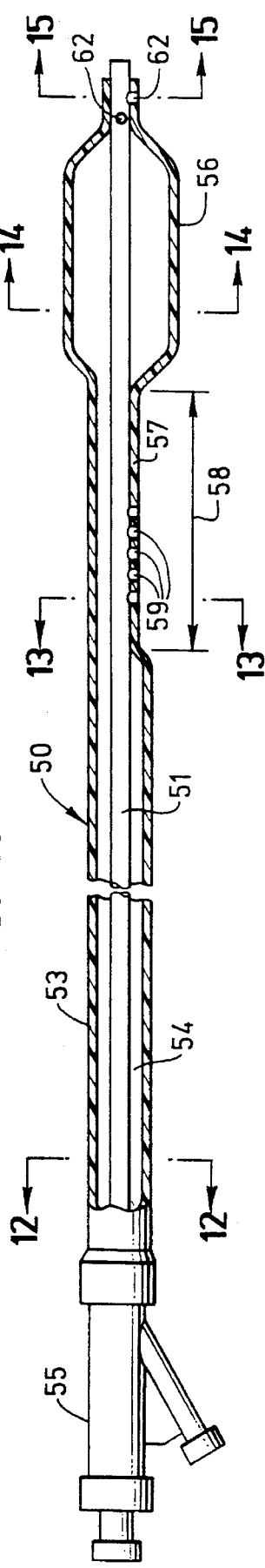 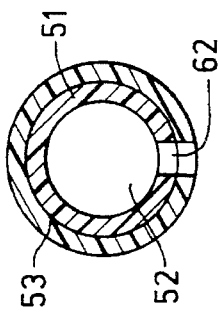 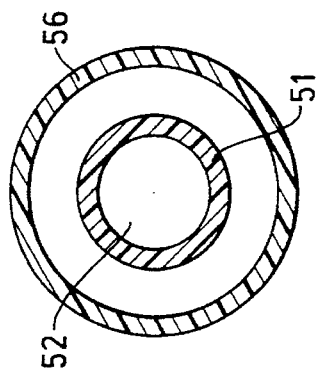 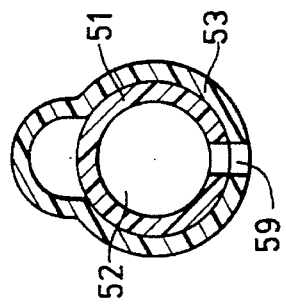 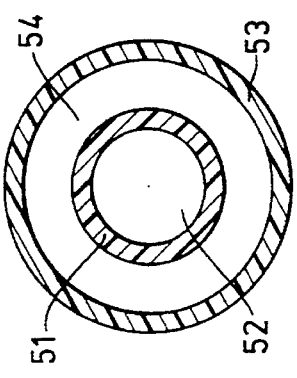

LOW PROFILE DILATATION CATHETER

RELATED APPLICATIONS

This is a continuation application of applications Ser. No. 08/095,814, which was filed on Jul. 20, 1993 now abandoned and Ser. No. 08/021,062, which was filed on Apr. 15, 1993, now abandoned both of which are continuation applications of application Ser. No. 07/700,617 filed on May 15, 1991 now abandoned.

BACKGROUND OF THE INVENTION

This invention generally relates to intravascular catheters, such as balloon dilatation catheters used in percutaneous transluminal coronary angioplasty (PTCA).

In classic PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from the proximal end to turn the distal tip of the guiding catheter so that it can be guided into the coronary ostium. A guidewire and a balloon dilatation catheter are introduced into and advanced through the guiding catheter to the distal tip thereof, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the balloon is inflated to a predetermined size with radiopaque liquid at relatively high pressures (e.g., generally 4–12 atmospheres) to dilate the stenosed region of the diseased artery. The balloon is then deflated so that the dilatation catheter can be removed from the dilated stenosis and blood flow will resume therethrough.

Further details of guiding catheters, dilatation catheters, guidewires, and other devices for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. 4,827,943 (Taylor et al.) which are hereby incorporated herein in their entirety by reference thereto.

Several notable improvements have recently been made in balloon angioplasty catheters. One such modification is described in U.S. Pat. No. 4,748,982 (Horzewski et al.) wherein a short sleeve or inner lumen at least about 10 cm in length is provided within the distal section of the catheter body which extends from a first port proximal to the balloon to a second port in the distal end of the catheter and which is adapted to slidably receive a guidewire. The proximal port is not less than about 10 cm and not more than about 40 cm from the distal end of the catheter. Preferably, a slit is provided in the catheter body extending from the proximal port to a location proximal to the proximal end of the balloon to facilitate the removal of the catheter from the proximal end of the guidewire which extends out of the patient.

Another modification, which was introduced into the market place by the assignee of the present application (Advanced Cardiovascular Systems, Inc.), provides a plurality of perfusion ports in the wall forming at least part of the catheter body proximal to the balloon. These perfusion ports are in fluid communication with an inner lumen extending to the distal end of the catheter body. A plurality of perfusion ports are preferably provided in the catheter body distal to the balloon which are also in fluid communication with the inner lumen extending to the distal end of the catheter body. When the balloon on the distal extremity of the dilatation catheter is inflated to dilate a stenosis, oxygenated blood in the artery or the aorta or both, depending upon the location of the dilatation catheter within the coronary anatomy, is forced to pass through the proximal perfusion ports, through the inner lumen of the catheter body and out the distal perfusion ports. This provides oxygenated blood downstream from the inflated balloon to thereby prevent or minimize ischemic conditions in tissue distal to the catheter. As is appreciated by those skilled in the art, tissue distal to a stenosis is frequently already in jeopardy due to ischemic conditions which may exist. As a result, care must be exercised in sizing the perfusion ports and the inner lumen to ensure that there is adequate flow of oxygenated blood to tissue distal to the catheter to eliminate or minimize ischemic conditions.

A major and continual thrust of development work in the field of intravascular catheters, particularly angioplasty catheters, has been to reduce the profile, i.e. transverse dimensions, of such catheters and to improve the flexibility thereof without detrimentally affecting the pushability, particularly in the distal portion of such catheters. A reduction in profile with no loss in pushability allow an intravascular catheter to be advanced much further into a patient's vasculature and to cross much tighter lesions in the case of angioplasty catheters.

Despite many advances in this field, the need for lower profile intravascular catheters having greater flexibility with little or no loss in pushability remains. The present invention satisfies this need.

SUMMARY OF THE INVENTION

The present invention is directed to an intravascular catheter having a low profile, particularly in the distal portion thereof, and having improved flexibility.

The intravascular catheter of the invention generally includes, at least in the distal portion thereof, an inner tubular member having an inner lumen extending therein and an outer tubular member disposed about the inner tubular member. In the distal portion a length of the outer tubular member is bonded to a substantial part of the inner surface or inner periphery thereof to the outer surface of the inner tubular member. At least about 5% to about 90%, preferably about 30% to about 80%, of the periphery of the outer tubular member is bonded to the underlying inner tubular member so that the bonded portion of the outer member takes the shape of the inner tubular member to which it is bonded. The unbonded portion of the outer tubular member along said length defines with the inner tubular member a longitudinally extending inner lumen. The bond need not be continuous and may be intermittent so long as a significant portion thereof is bonded. The bonded section may extend along essentially the entire length of the catheter but should not be less than about 5 mm. Preferably, the length of the bonded section is about 10 cm to about 40 cm. The catheter is provided with a diagnostic or treatment means such as an inflatable dilatation balloon for angioplasty distal to the bonded section.

By bonding a length of the outer tubular member in the distal portion of the catheter to the exterior of the inner member, the profile of the catheter body in at least one transverse dimension in that area is reduced substantially to thereby provide improved flexibility. Moreover, the bonded portions of the inner member and the outer tubular members support one another thereby providing improvements in the pushability of the catheter. Substantial reductions in only one transverse dimensions can provide substantial improvements is flexibility. Minimum cross-sectional dimensions of the small diameter section of the outer tubular member for coronary dilatation catheters are on the order of about 0.02 to about 0.06 in.(0.51–1.5 mm). For peripheral arteries this dimension may be larger. The pushability of the reduced diameter bonded section of the catheter body is also frequently improved.

The improvements of the invention are applicable to a wide range of intravascular catheters and particularly to essentially all types of dilatation catheters with inflatable or expandable members, such as those described in the patents incorporated herein by reference. These and other advantages of the invention will become more apparent from the following detailed description of the invention when taken in conjunction with accompanying exemplary drawings.

BRIEF DESCRIPTION OF THE DRAWINGS

FIG. 1 is an elevational view, partially in section, of a balloon dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is an elevational view, partially in section, of another dilatation catheter embodying features of the invention.

FIG. 7 is a transverse cross-sectional view of the catheter shown in FIG. 6 taken along the lines 7—7.

FIG. 8 is a transverse cross-sectional view of the catheter shown in FIG. 6 taken along the lines 8—8.

FIG. 9 is a transverse cross-sectional view of the catheter shown in FIG. 6 taken along the lines 9—9.

FIG. 10 is a transverse cross-sectional view of the catheter shown in FIG. 6 taken along the lines 10—10.

FIG. 11 is an elevational view, partially in section, of another dilatation catheter embodying features of the invention.

FIG. 12 is a transverse cross-sectional view of the catheter shown in FIG. 11 taken along the lines 12—12.

FIG. 13 is a transverse cross-sectional view of the catheter shown in FIG. 11 taken along the lines 13—13.

FIG. 14 is a transverse cross-sectional view of the catheter shown in FIG. 11 taken along the lines 14—14.

FIG. 15 is a transverse cross-sectional view of the catheter shown in FIG. 11 taken along the lines 15—15.

DETAILED DESCRIPTION OF THE INVENTION

FIGS. 1–5 schematically illustrate an over-the-wire dilatation catheter embodying features of the invention. The catheter includes an elongated catheter body 10 which has an inner tubular member 11 with an inner lumen 12, an outer tubular member 13 disposed about the inner tubular member and defining therebetween an annular inner lumen 14 which extends through the proximal portion of the catheter body. An adapter 15 is secured to the proximal ends of the inner and outer tubular members 11 and 13. A relatively inelastic, inflatable balloon 16 is formed as part of the outer tubular member 13 with the distal end of the balloon secured to the distal end of the inner tubular member 11. The balloon 16 may be formed from the same tubing as the outer tubular member 13 as shown in FIG. 1 or it may be made separately and secured to the distal end of the outer tubular member as shown in FIGS. 6 and 11.

The outer tubular member 13 generally has a distal section 17 with small transverse dimensions in at least one direction, preferably smaller than an adjacent portion of the outer tubular member. As best shown in FIGS. 1 and 3, a length 18 of the small diameter distal section 17 is bonded to the exterior of the inner tubular member 11 with a significant portion of the periphery outer member, typically about 50% to about 80%, being bonded to the inner member. The unbonded portion 19 of the distal section 17 along the length 18 forms an inflation lumen 20 which is in fluid communication with the interior of the balloon 16 and the annular lumen 14.

The use of the dilatation catheter shown in FIGS. 1–5 generally follows conventional PTCA practices with over-the-wire dilatation catheters. A guidewire 21 is backloaded into the inner lumen 12 of the inner tubular member 11 of the catheter body 10 and both the guidewire and the catheter are advanced together through a guiding catheter (not shown) which has been previously disposed within the patient's arterial system, with the distal end of the guiding catheter seated within the ostium of the desired coronary artery. The guidewire 21 is advanced out the distal end of the guiding catheter into the patient's coronary anatomy until it crosses the lesion to be dilated, and then the dilatation catheter is advanced over the guidewire which is being held in its position, until the balloon 16 on the dilatation catheter is properly disposed within the stenotic region so that the lesion is dilated upon the inflation of the balloon. After the dilatation, the balloon 16 is deflated and the catheter and the guidewire are withdrawn from the patient. If further treatment or diagnosis is to be conducted, the guidewire can be replaced with an exchange wire before removing the dilatation catheter so that the first catheter can be removed and another advanced into the desired location or an extension wire can be attached to the proximal end of the guidewire in place to perform essentially the same function. See the discussion of exchange wires and extension wires in U.S. Pat. No. 4,827,941 (Taylor et al.) which has been incorporated herein by reference.

FIGS. 6–10 schematically illustrate another dilatation catheter embodying features of the invention which is quite similar in its distal structure to the embodiment shown in FIGS. 1–5. In the embodiment shown in FIGS. 6–10, the catheter body 30 includes an outer tubular member 31 which has a two layered proximal portion 32 which has an outer plastic tubular element 33 which fits tightly, e.g. is shrunk fit, onto an inner tubular element 34, an adapter 35 is secured to the proximal end of the catheter body. The outer plastic tubular element 33 extends beyond the distal end of the inner tubular element 34 and a relatively inelastic balloon 36 is secured by its proximal end to the distal end of the outer plastic element 33 of the outer tubular member 31. The distal end of the balloon 36 is bonded to the distal end of the inner tubular member 37. The outer plastic tubular element 33 of the outer tubular member 31 has a distal section 38 which is an extension of the outer plastic element with small dimensions in at least one transverse direction as in the previously described embodiment. A significant portion of the interior surface of the distal section 38 along the length 39 is bonded to the exterior of the inner tubular member 37. To this extent, the distal end of this embodiment is quite similar to the embodiment shown in FIGS. 1–5. The inner tubular member 37 of this embodiment is quite short compared to the inner tubular of the embodiment shown in FIGS. 1–5.

In the embodiment shown in FIGS. 6–10, the catheter body 30 is provided a guidewire port 40 which passes through the bonded walls 41 and 42 of the inner and outer tubular members 37 and 31 respectively and which is in communication with a relatively short inner lumen 43 extending within the distal portion of the inner tubular member 37. Guidewire 44 extends proximally through the inner lumen 43 and out the proximal port 40. The coil 45 on the distal end of the guidewire 44 extends out the distal port 46 in the distal end 47 of the catheter body 30. The inner tubular element 34 onto which the outer plastic tubular element 33 is secured is preferably hypotubing and may be formed of stainless steel or a NiTi alloy, particularly a NiTi alloy with superelastic properties, such as described in co-pending application Ser. No. 07/629,381, filed Dec. 18, 1990, entitled Superelastic Guiding Member and assigned to the present assignee, Advanced Cardiovascular Systems, Inc. At the distal extremity of the inner tubular element 34, the upper portion thereof is removed to expose the inner lumen 48 to the interior of the balloon 36 to allow inflation fluid to be directed thereto. It is presently preferred to secure the proximal end of the inner tubular member 37 to the lower portion of the distal extremity of the inner tubular element or hypotubing by heat shrinking the outer plastic tubular element 33 onto the inner tubular element with the flattened end of the inner tubular member disposed therebetween. The catheter construction of this embodiment with a relatively short inner lumen which is adapted to slidably receive a guidewire therein eliminates the need for using an exchange wire or a guidewire extension. A slit 49 is preferably provided in the bonded portions of the inner and outer tubular members 37 and 31 extending from the guidewire port 40 to a location adjacent the proximal end of the balloon 36. The slit 49 greatly facilitates the removal of the catheter from the proximal end of the guidewire 44 when the catheter is to be replaced or exchanged for another catheter and it also eliminates the need for using a guidewire extension or an exchange wire as described in Horzewski et al., which has been incorporated herein by reference. A dual lumen type construction such as described in Horzewski et al. may also be used in the portion of the catheter proximal to the guidewire port 40.

There are at least two modes of inserting the dilatation catheter of this embodiment into the patient's coronary anatomy. The first method is for the most part the same as in the prior embodiment, namely, the guidewire 44 is preloaded into the short inner lumen 43 of the inner tubular member 37 of the catheter body 30 and both are advanced through a guiding catheter (not shown) previously disposed within the patient's arterial system with the distal end of the guiding catheter seated within the ostium of a coronary artery. The second mode, frequently called the "bare wire" technique, involves first advancing a guidewire 44 through arid out the guiding catheter until it is positioned within the patient's coronary artery across the lesion to be dilated. The proximal end of the guidewire 44, which is outside the patient, is backloaded, i.e. inserted into the short inner lumen 43 of the inner tubular member 37 and advanced proximally therein until it exits the guidewire port 40. The proximal end of the guidewire 44 is held in place and the catheter is advanced over the guidewire through the patient's vascular system until the dilatation balloon 36 on the catheter is positioned across the stenotic region so that the stenosis can be dilated upon the inflation of the balloon. After the dilatation of the lesion, the balloon 36 is deflated and the catheter may be removed from the patient's artery. If other treatments are necessary, the catheter is slidably removed over the guidewire 44, leaving the guidewire in place so that other catheters can be advanced over the in-place guidewire in a similar manner without the need for exchange wires or guidewire extensions.

FIGS. 11 through 15 illustrate yet another dilatation catheter embodying features of the invention which provides for the perfusion of blood distal to the catheter during the dilatation of a stenotic lesion. The catheter includes the catheter body 50, an inner tubular member 51 which has an inner lumen 52, an outer tubular member 53 which is disposed about the inner tubular member and which defines an annular lumen 54 located between the inner and outer tubular members, an adapter 55 secured to the ends of the inner and outer members, and a relatively inelastic balloon 56 which is secured by its proximal end to the distal end of the outer tubular member 53 and by its distal end to the distal end of the inner tubular member 51. The outer tubular member 53 has a distal section 57 a length of 58 of which is bonded to the exterior of the inner tubular member 51 as previously described in the first two embodiments of the invention. The above-described portion of this embodiment has essentially the same structure as the embodiments shown in FIGS. 1–10.

The dilatation catheter shown in FIGS. 11–15 differs from the other embodiments in that it has a plurality of perfusion ports 59 proximal to the balloon 56 which pass through the bonded walls 60 and 61 of the inner and outer tubular members 51 and 53 respectively and which are in fluid communication with the inner lumen 52 of the inner tubular member 51. Additionally, one or more perfusion ports 62 are provided distal to the balloon 56 through the wall 60 of the inner tubular member 51 and are in fluid communication with the inner lumen 52 extending therein. In this manner, when the balloon 56 is inflated during an angioplasty procedure within a patient's vasculature, oxygenated blood is forced to pass through the proximal perfusion ports 59, through the inner lumen 52 and then out the distal perfusion ports 62 to provide oxygenated blood distal to the catheter and thereby avoid the generation of ischemic conditions in tissue downstream thereof. The transverse dimensions of the inner tubular member 51 within the bonded section are preferably larger than in the embodiments previously discussed to allow for an increased flow of blood therethrough.

The use of the embodiment shown in FIGS. 11–15 is essentially the same as the embodiment shown in FIGS. 1–5. The only essential difference is that the balloon 56 can be inflated for significantly longer periods, e.g. typically about 20–30 minutes but possibly up to 5 hours or more, than the first described embodiment because oxygenated blood is flowing to the tissue distal to the inflated balloon.

The dilatation catheter shown in FIGS. 11–15 may be modified by providing a guidewire port at the proximal end of the section 58, proximal to the portion of the small diameter distal section 57 in which the proximal perfusion ports 59 are located. However, the guidewire port should be spaced sufficiently far proximally from the portion of the bonded distal section 57 having the perfusion ports 59 so that the guidewire can be pulled proximally and remain within the inner lumen 52 while the balloon 56 is inflated during the dilatation but not interfere with the flow of blood through the perfusion ports 59 and 62 and the inner lumen 52. After the angioplasty procedure is completed, the guidewire can then be advanced distally through the inner lumen 52 and out the distal end thereof in order to maintain access to the lesion in case further treatment or diagnosis is necessary or desirable.

The use of the catheter with both perfusion ports and a guidewire port as described above is essentially the same as the use of the dilatation catheter illustrated in FIGS. 5–10, but with the additional advantage that long term dilatations are possible.

The above described catheters may be made by conventional techniques well known to those skilled in the art. Many suitable techniques are described in the references incorporated herein. The small diameter distal sections 17, 38 and 57 may be formed by heat shrinking the portion of the outer tubular members 13, 31 and 53 which form the distal sections onto the underlying inner members 11, 37 and 51. A mandrel (not shown) is disposed in the space between the inner and outer tubular members 11, 37 and 51 and 13, 31 and 53 so that upon the heat shrinking of the outer tubular member an inflation lumen is formed through the distal sections which is in fluid communication with the lumen in the proximal portion of the catheter body and the interior of the balloon 16. This bonds the small dimensioned distal section to the inner tubular member. A mandrel may be inserted into the inner lumen of the inner tubular member to support the latter during the heat shrinking of the outer tubular member thereon. Alternate methods may be employed to make the small dimensioned distal section. For example, the small dimensioned distal section 17 may be preformed and then be adhesively bonded to the exterior of the inner tubular member. Multiple lumens similar to the inflation lumen may be formed in the small dimensioned section, such as the top and bottom thereof, by employing multiple mandrels when heat shrinking the outer tubular member onto the exterior of the inner tubular member.

The various components of the catheters and guidewires of the invention can be formed from a wide variety of conventional materials. The inner and outer plastic tubular members may be made from polyethylene, polyimide, polyvinyl chloride and other suitable plastic materials. The hypotubing may be formed of stainless steel, NiTi superelastic alloys or other suitable materials. Composite materials such as described in co-pending application Ser. No. 07/241,047, filed Sep. 6, 1988 (which is incorporated herein by reference thereto) may also be used. The balloon may be made from polyethylene, polyethylene terephthalate and other relatively inelastic polymers and other materials.

The dimensions of the catheters generally follow the dimensions of conventional intravascular catheters. For coronary use the length is typically about 135 cm and the outer diameter of the outer tubular member is about 0.02 to about 0.06 inch. In a presently preferred embodiment, the small dimensioned distal section is long enough (e.g. preferably about 10 to about 40 cm) to ensure that it is the only portion of the catheter body proximal to the balloon which exits the guiding catheter and enters the patient's coronary anatomy during intravascular procedures. The transverse dimensions of the catheter may be larger with catheters for use in peripheral arteries and other locations.

While the invention has been described herein primarily in terms of catheters for coronary angioplasty, the invention may be employed in a wide variety of catheters for insertion into various body lumens. Additionally, modifications and improvements can be made to the invention without departing from the scope thereof.

What is claimed is:

1. An elongated catheter for performing an intravascular procedure comprising:

a) an elongated catheter shaft which has a distal section with an inner tubular member having a first inner lumen and a distal end with a port in communication with the first inner lumen and an outer tubular member disposed about the inner tubular member having about 30% to about 90% of the inner periphery thereof along a length of the distal section of at least about 10 cm taking the shape of and being secured to the exterior of the inner tubular member and the outer tubular member having along said length a portion unsecured to the exterior of the inner tubular member, being longitudinally off-set and coextensive with the portion secured and having a second inner lumen extending longitudinally between the inner tubular member and the unsecured portion of the outer tubular member, a transverse cross-section of the distal section along the said length being substantially larger in a first direction than in a second direction perpendicular to the first direction; and b) means for performing a vascular procedure on the catheter shaft at a location distal to at least a portion of said length.

2. The elongated catheter of claim 1 wherein at least one perfusion port extends through secured walls of the outer tubular member and the inner tubular member and is in fluid communication with the inner lumen of the inner tubular member.

3. The elongated catheter of claim 2 wherein at least one perfusion port is provided in the inner tubular member distal to the balloon which is in fluid communication with the inner lumen thereof.

4. The elongated catheter of claim 1 wherein at least about 30% to about 80% of the inner periphery of the section of the outer tubular member is bonded to the exterior of the inner tubular member.

5. The elongated catheter of claim 1 wherein a portion of the inner tubular member proximal to the portion thereof which is secured to the outer tubular member in the distal shaft section is formed of hypotubing.

6. The elongated catheter of claim 1 including an inflatable balloon at a location distal to the secured section and having an interior in fluid communication with the second inner lumen.

7. The elongated catheter of claim 1 wherein a portion of the inner tubular member proximal to the portion thereof secured to the outer tubular is provided with a stiffening member.

8. The elongated catheter of claim 7 wherein the stiffening member is a stiffening mandrel and is disposed within the inner lumen of the inner tubular member.

9. The elongated catheter of claim 1 including a guidewire receiving port which is located proximal to the means for performing an intravascular procedure and which is in communication with the inner lumen of the inner tubular member.

10. A balloon dilatation catheter for performing an angioplasty procedure within a patient's arterial system comprising:

a) an elongated catheter body having
   an inner tubular member with a first inner lumen extending therethrough and a distal end with a port in fluid communication with the first inner lumen, both of which are adapted to slidably receive a guidewire therein, and
   an outer tubular member which is disposed about the inner tubular member and which has a length of at least about 10 cm in a distal portion of the catheter body with about 30% to about 90% of an inner periphery thereof along the length taking the shape of and being secured to the exterior of an underlying portion of the inner tubular member and with portion of the outer tubular member along the length being unsecured to the inner tubular member and providing a passageway which is in fluid communication with an inflation port at a location proximal to the distal end, the outer tubular member in the length where secured to the inner tubular member having a transverse cross-sectional dimension in a first direction being substantially larger than a transverse cross-sectional dimension in a second direction perpendicular to the first direction;

b) an inflatable dilatation balloon on the elongated catheter shaft which is distal to the portion of the outer tubular member secured to the inner tubular member and which has an interior in fluid communication with the passageway through the inflation port and which has a distal end sealingly secured to a distal portion of the inner tubular member extending through the interior of the balloon; and c) means on the proximal end of the catheter shaft to direct inflation fluid from a source through the passageway into the interior of the inflatable dilatation balloon.

11. The dilatation catheter of claim 10 wherein not more than about 80% of the inner periphery of the outer tubular member takes the shape of and is secured to the exterior of the inner tubular member along the length thereof secured to the inner tubular member.

12. The dilatation catheter of claim 11 wherein the portion of the outer tubular member secured to the outer periphery of the inner tubular member has a length of not more than about 40 cm.

13. The dilatation catheter of claim 10 wherein a guidewire receiving port extends through the secured portions of the inner tubular member and the outer tubular member and is in communication with the inner lumen of the inner tubular member.

14. The dilatation catheter of claim 10 wherein at least one perfusion port extends through the secured portions of the inner tubular member and the outer tubular member and is in communication with the inner lumen of the inner tubular member.

15. The dilatation catheter of claim 14 wherein at least one perfusion port is provided in the inner tubular member distal to the balloon which is in communication with the inner lumen thereof.

16. The dilatation catheter of claim 10 wherein a portion of the inner tubular member proximal to the portion thereof secured to the outer tubular is provided with a stiffening element.

17. The dilatation catheter of claim 16 wherein a portion of the inner tubular member proximal to the portion thereof which is secured to the outer tubular member is formed of hypotubing to increase the stiffness of the inner tubular member.

18. The dilatation catheter of claim 16 wherein the stiffening member is a mandrel which is disposed within the inner lumen of the inner tubular member.

19. A balloon dilatation catheter for performing angioplasty procedures within a patient's arterial system, comprising:

a) an elongated catheter body having
   an inner tubular member with an inner lumen extending therethrough, which is relatively short in comparison with the elongated catheter body, and a distal end with a first port in communication with the inner lumen, both of which are adapted to slidably receive a guidewire therein, and
   an outer tubular member which is disposed about the inner member and which has a length of at least about 10 cm in the distal portion of the catheter body having about 30% to about 90% of an inner periphery thereof taking the shape of and being secured to an outer periphery of an underlying portion of the inner tubular member and a portion of the outer tubular member not secured to the outer periphery of the inner tubular member providing a passageway which is in fluid communication with an inflation port at a location proximal to the distal end, the outer tubular member along said length having a first transverse cross-sectional dimension in a first direction which is substantially larger than in a second transverse cross-sectional dimension in a second direction perpendicular to the first direction;

b) an inflatable dilatation balloon located on a distal portion of the catheter shaft;

c) a second guidewire port which is disposed proximal to the inflatable dilatation balloon and which is in communication with the inner lumen of the inner tubular member; and d) means to direct inflation fluid from a source through the passageway between the portion of the outer tubular member which is not secured to the inner tubular member along said length and the underlying inner tubular member into the interior of the balloon.

20. The dilatation catheter of claim 19 wherein not more than about 80% of the inner periphery of the outer tubular member along said length takes the shape of and is secured to the outer periphery of the inner tubular member.

21. The balloon dilatation catheter of claim 19 wherein the portion of the outer tubular member secured to the outer periphery of the inner tubular member has a length of not more than about 40 cm.

22. The dilatation catheter of claim 19 wherein not more than about 80% of the inner periphery of the secured length of the outer tubular member takes the shape of and is secured to the exterior of the inner tubular member.

23. The dilatation catheter of claim 19 wherein the catheter body has a relatively stiff proximal portion and a relatively flexible distal portion.

24. The dilatation catheter of claim 19 wherein the proximal portion of the outer tubular member is hypotubing.

25. A balloon dilatation catheter for performing angioplasty procedures within a patient's arterial system, comprising:

a) an elongated catheter body having an inner tubular member with an inner lumen extending therein and an outer tubular member which is disposed about the inner tubular member and which has a length of at least about 10 cm in a distal portion of the catheter body having about 30% to about 90% of an inner periphery thereof taking the shape of and being secured to an outer periphery of an underlying portion of the inner tubular member and a passageway disposed between a portion of the outer tubular member not secured to the outer periphery of and the inner tubular member along said length, the outer tubular member along said length having a transverse cross-sectional dimension in a first direction which is substantially larger than a transverse cross-sectional dimension in a second direction perpendicular to the first direction;

b) an inflatable dilatation balloon on a distal portion of the catheter body which has a distal end secured to the distal end of the inner tubular member which extends through the interior of the balloon;

c) at least one perfusion port which extends through walls of the inner and outer tubular members secured together and which is in communication with the inner lumen of the inner tubular member; and d) means to direct inflation fluid from a source through the passageway between the the outer tubular member and the inner tubular member and into the interior of the balloon.

26. The elongated catheter of claim 25 wherein the portion of the outer tubular member secured to the outer periphery of the inner tubular member has a length of not more than about 40 cm.

27. An elongated dilatation catheter for performing angioplasty procedures comprising:

a) an elongated catheter shaft with a flexible distal section having a length of about 10 to about 40 cm, having a first longitudinally extending inner lumen in fluid communication with a port in the distal end of the catheter shaft, wherein both the inner lumen and the port are adapted to receive a guidewire, a second inner lumen which extends longitudinally and generally parallel with the first inner lumen, with one transverse dimension of the catheter shaft in the distal section in a first direction being substantially larger than a second transverse dimension of the catheter shaft in the distal section in a second direction perpendicular to the first direction, one of the inner lumens being disposed above the other inner lumen in the direction of the larger dimension; and b) inflatable means for dilating a stenosis which has an interior in fluid communication with the second inner lumen and which is mounted on a distal portion of the catheter shaft.

28. An elongated catheter for performing an intravascular procedure comprising:

a) an elongated catheter shaft with a flexible distal section having a length of at least about 10 cm, having a first longitudinally extending inner lumen in fluid communication with a port in the distal end of the catheter shaft, wherein both the inner lumen and the port are adapted to receive a guidewire, a second inner lumen which extends longitudinally and generally parallel with the first inner lumen, with one transverse dimension of the catheter shaft in the distal section in a first direction being substantially larger than a second transverse dimension of the catheter shaft in the distal section in a second direction perpendicular to the first direction, one of the inner lumens being disposed above the other inner lumen in the direction of the larger transverse dimension; and b) means for performing an intravascular procedure on a distal portion of the catheter shaft proximal to the distal end thereof.

* * * * *

UNITED STATES PATENT AND TRADEMARK OFFICE
CERTIFICATE OF CORRECTION

PATENT NO.  : 5,496,275
DATED       : March 5, 1996
INVENTOR(S) : Motasim M. Sirhan and Jovito L. Fernando It is certified that error appears in the above-indentified patent and that said Letters Patent is hereby corrected as shown below:

Col. 9, line 58, after "tubular", add --member--.

Signed and Sealed this

Eleventh Day of June, 1996

Attest:

BRUCE LEHMAN

Attesting Officer

Commissioner of Patents and Trademarks